United States Patent [19]

Sachdev

[11] 4,278,814
[45] Jul. 14, 1981

[54] PREPARATION OF 2-METHYLENE-1,3-PROPANEDIAMIDE BY A FLUORIDE ANION-INITIATED β-ELIMINATION REACTION

[75] Inventor: Krishna G. Sachdev, Beacon, N.Y.

[73] Assignee: Polaroid Corporation, Cambridge, Mass.

[21] Appl. No.: 109,812

[22] Filed: Jan. 7, 1980

[51] Int. Cl.$^3$ .................. C07C 102/00; C07F 7/08
[52] U.S. Cl. ............................. 564/160; 556/419
[58] Field of Search .......... 260/561 A, 561 K, 561 N; 556/419; 564/160

[56] References Cited

U.S. PATENT DOCUMENTS

| | | | |
|---|---|---|---|
| 2,466,395 | 4/1949 | Dickey | 260/78.5 |
| 2,741,631 | 4/1956 | Sauer | 260/561 N |
| 2,774,778 | 12/1956 | Sommer | 556/419 |
| 3,247,280 | 4/1966 | Kanner | 260/561 A |
| 3,546,270 | 12/1970 | Kirchmayr et al. | 260/561 N |

FOREIGN PATENT DOCUMENTS 679812  2/1964  Canada ..................... 556/419

OTHER PUBLICATIONS

Eberson Acta Chem. Scand. 10 (1956) pp. 633–637.
R'Jarvie Organom et al. Chem. Rev. A 6 (1970) pp. 153–207.
Cunico et al. J. Am. Chem. Soc. 94 (1972) p. 2868.
Chan et al. Tet. Lett. 1974 #2 p. 171.
Chan et al. Tet. Lett. 1974 #39 p. 3511.

*Primary Examiner*—Arthur P. Demers
*Attorney, Agent, or Firm*—John J. Wasatonic

[57] ABSTRACT

A process for preparing 2-methylene-1,3-propanediamide is disclosed which comprises providing a solution of a compound of the formula

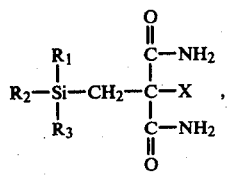

wherein $R_1$, $R_2$, and $R_3$ can each independently be lower alkyl of from 1 to 10 carbon atoms, aryl, alkaryl, aralkyl, or halogen and X is an electron-accepting leaving group, in an inert, aprotic organic solvent, and subjecting the compound in solution to fluoride anion to effect elimination of the silyl group

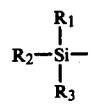

and the electron-accepting leaving group

—X from the compound to form a double bond between those carbon atoms to which the silyl group and the electron-accepting leaving group were bonded, thereby forming 2-methylene-1,3-propanediamide. 2-Methylene-1,3-propanediamide is useful in preparing polymers which can be used in preparing coating compositions, films, and filaments.

17 Claims, No Drawings

PREPARATION OF 2-METHYLENE-1,3-PROPANEDIAMIDE BY A FLUORIDE ANION-INITIATED β-ELIMINATION REACTION

BACKGROUND OF THE INVENTION

This invention relates to the preparation of 2-methylene-1,3-propanediamide. More particularly, it relates to a process for preparing this monomer by a fluoride anion initiated β-elimination reaction conducted in the presence of an inert, aprotic organic solvent.

U.S. Pat. No. 2,466,395, issued to J. B. Dickey, discloses the use of 2-methylene-1,3-propanediamide or, more commonly, methylene malonamide, as a comonomer for preparing copolymers useful in preparing films and filaments. The process for preparing this monomer, disclosed therein, is said to comprise a sulfuric acid or hydrogen peroxide hydrolysis of 2-methylene-propanedinitrile, i.e.,

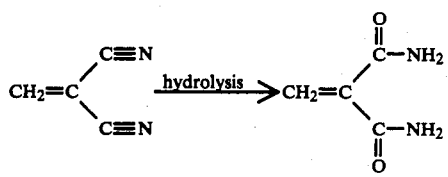

This preparative method has certain inherent disadvantages. One disadvantage is that 2-methylene-1,3-propanediamide tends to be unstable in the presence of such reagents as sulfuric acid and hydrogen peroxide, the monomer tending to undergo polymerization or other degradative reactions in the presence of such reagents. Thus, the reaction conditions suggested by U.S. Pat. No. 2,466,395 for preparing this monomer are generally unfavorable in terms of obtaining the desired product and especially in terms of obtaining a high yield of the desired product.

Another disadvantage of the process disclosed in U.S. Pat. No. 2,466,395 is that 2-methylenepropanedinitrile is highly toxic and, as such, is an undesirable intermediate.

A particularly useful process for preparing 2-methylene-1,3-propanediamide, which avoids the aforementioned problems and disadvantages, forms the subject matter of copending U.S. Patent application Ser. No. 109,811 of Howard C. Hass, et al filed Jan. 7, 1980. As disclosed therein, 2-methylene-1,3-propanediamide can be prepared by providing a solution of a 1,3-propanediamide, substituted at the 2-carbon atom with a trisubstituted silyl methyl group and an electron-accepting leaving group, in an inert, aprotic organic solvent and subjecting the compound in the solution to β-elimination reaction conditions sufficient to eliminate the trisubstituted silyl group and the electron-accepting leaving group from the compound to form a double bond between the carbon atoms to which the trisubstituted silyl group and the electron-accepting leaving group were bonded. The present invention relates to an improved process for the preparation of 2-methylene-1,3-propanediamide by a fluoride anion-initiated β-elimination reaction.

SUMMARY OF THE INVENTION

The present invention provides a novel process for preparing the monomer 2-methylene-1,3-propanediamide which comprises providing a solution of a compound of the formula

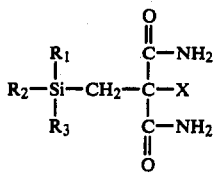

where $R_1$, $R_2$, and $R_3$ each can independently be lower alkyl of from 1 to 10 carbon atoms, aryl, alkaryl, aralkyl, or halogen, in an inert, aprotic organic solvent, and subjecting the compound in solution to fluoride anion to effect elimination of the silyl group

and the electron-accepting leaving group

—X from the compound to form a double bond between those carbon atoms to which the silyl group and the electron-accepting leaving group were bonded, thereby forming 2-methylene-1,3-propanediamide. It has been found that the conduct of this β-elimination process permits formation of 2-methylene-1,3-propanediamide in high yield and with minimized polymerization or derivatization thereof.

For a fuller understanding of the present invention, reference should be had to the following detailed description.

DETAILED DESCRIPTION OF THE INVENTION

Preparation of 2-methylene-1,3-propanediamide tends to be difficult because of the high reactivity of this monomer. For example, it has been found to be sensitive to protic materials whereby the monomer is derivatized by addition of the protic material across the double bond, e.g.,

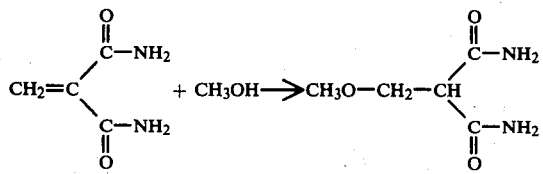

Such derivatization reactions are generally also accompanied by some degree of polymerization of the monomer. In addition, the monomer has been found to readily undergo anionic and free radical polymerization reactions such that preparation and isolation of the monomer without a substantial degree of concurrent polymerization tends to be difficult.

The present invention provides a novel process for preparing 2-methylene-1,3-propanediamide which avoids hydrolysis reaction conditions and permits formation of the desired monomer in high yield with minimized derivatization or polymerization thereof.

The process of the present invention comprises providing a solution of a compound of the formula

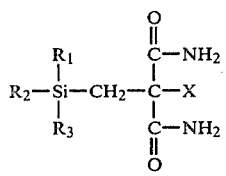

where $R_1$, $R_2$ and $R_3$ each can independently be lower alkyl of from 1 to 10 carbon atoms, aryl, alkaryl, aralkyl, or halogen, and X is an electron-accepting leaving group, in an inert aprotic organic solvent, and subjecting the compound in solution to fluoride anion to effect elimination of the silyl group

and the electron-accepting leaving group $$-X$$

from the compound to form a double bond between those carbon atoms to which the silyl group and the electron-accepting leaving group were bonded, thereby forming 2-methylene-1,3-propanediamide.

The removal of the silyl group and the electron-accepting leaving group situated $\beta$ thereto from the starting material to form the desired carbon-carbon double bond constitutes a $\beta$-elimination reaction. Thus, by the term "$\beta$-elimination reaction" is meant a reaction involving the elimination or removal of two groups from a parent molecule, said groups being substituted on the parent molecule on adjacent carbon atoms, i.e., $\beta$ to each other, with the elimination or removal resulting in the formation of a double bond between the adjacent carbon atoms.

According to the present invention, a starting material of the formula

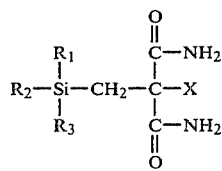

undergoes a $\beta$-elimination reaction to produce 2-methylene-1,3-propanediamide when subjected to fluoride anion in the presence of an inert, aprotic organic solvent. It has been found that initiation of the $\beta$-elimination reaction by fluoride anion in such a solvent permits production of 2-methylene-1,3-propanediamide in high yield with minimized derivatization or polymerization thereof.

The fluoride anion can be provided by dissolving in the inert, aprotic organic solvent any inorganic or organic fluoride salt capable of ionizing therein to provide fluoride anion. Ionizable fluoride salts suitable for use in the present invention include alkali metal fluoride salts such as potassium fluoride and sodium fluoride, and quaternary ammonium fluoride salts such as tetramethylammonium fluoride, tetraethylammonium fluoride, tetrapropylammonium fluoride, and tetrabutylammonium fluoride.

It has been found that the use of fluoride anion as an initiating agent permits the conduct of the $\beta$-elimination reaction at relatively low temperatures. In particular, it has been found that the reaction can be conducted at a temperature of from about 15° C. to about 50° C. A preferred reaction temperature range is about 20° C. to about 35° C., the reaction proceeding with facility in this range to produce the monomer in high yield.

In view of the above described reactivity of 2-methylene-1,3-propanediamide, it will be appreciated that the production of this monomer at low reaction temperatures is advantageous in that the tendency of the monomer to undergo derivatization or polymerization is minimized. Moreover, conduct of the desired reaction at relatively low reaction temperatures permits more efficient large-scale production of the desired product consistent with the objectives of minimizing derivatization and polymerization reactions. In contrast, conducting the reaction at the elevated temperatures required by other means of $\beta$-elimination initiation, such as thermally initiating the reaction at a temperature of from 80° C. to 110° C., increases the tendency of the monomer to undergo derivatization or polymerization. Thus, fluoride anion initiation of the $\beta$-elimination reaction, within the above specified temperature ranges, presents advantages over the conduct of the reaction at more elevated temperatures in that degradative side reactions are minimized and higher yields of the desired product can be more readily obtained.

The advantages resulting from the use of fluoride anion are realized in the present invention notwithstanding the anionic nature of this initiating agent which might be expected to cause substantial derivatization of polymerization of the monomer. It has been found, however, that fluoride anion is an efficient initiating agent for the $\beta$-elimination reaction and that possible degradative side reactions occur, if at all, to a minimized degree.

In carrying out the process of the present invention, the fluoride anion can be present in an amount corresponding to a molar ratio of fluoride anion to starting material of about 0.1:1.0 to about 2.0:1.0. It has been found that optimum yields are obtained when the fluoride anion is present in moderate excess, on a molar basis, over the starting material. Accordingly, a molar ratio of fluoride anion to starting material of about 1.1:1.0 to about 1.5:1.0 is preferred.

The substituents on the silicon atom, $R_1$, $R_2$, and $R_3$ can each independently be lower alkyl of from 1 to 10 carbon atoms (e.g., methyl, ethyl, propyl, isopropyl); aryl (e.g., phenyl, naphthyl); alkaryl (e.g., tolyl); aralkyl (e.g., benzyl); or halogen (e.g., chloro, bromo, iodo). In a preferred embodiment of the present invention, each of $R_1$, $R_2$, and $R_3$ is lower alkyl of from 1 to 10 carbon atoms. Most preferably, each of $R_1$, $R_2$, and $R_3$ is methyl. It will be appreciated that methyl groups provide minimal steric interference about the silicon atom as compared to that provided by more bulky substitutents. Such steric interference may have an affect on the rate of reaction since the reaction is believed to involve an interaction between the silicon atom and the fluoride anion.

The leaving group X can be any group capable of accepting electrons from the starting material such that cleavage of the C—X bond occurs to effect removal or elimination of X from the starting material. Suitable electron-accepting leaving groups include chloride, bromide, and iodide; hydroxy; alkoxy; thiol; thioethers; sulfonyl, in particular, p-toluenesulfonyl; quaternary nitrogen groups; phosphonium groups; and

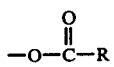

wherein R can be alkyl or aryl. The particular leaving group used is not critical provided that it is capable of departing from the starting material with the bonding electron pair. A study of electron-accepting leaving groups is provided by C. J. M. Stirling, Acc. Chem. Res., 12, 198 (1979).

A preferred electron-accepting leaving group from a preparative standpoint is chloride. It has been discovered that chloride is readily eliminated from the starting material under the reaction conditions of the present process.

The process of the present invention is conducted in the presence of an inert, aprotic organic solvent. Such a solvent system is necessary due to the aforementioned tendency of the product 2-methylene-1,3-propanediamide to add protic solvents and reagents across the double bond and/or to undergo polymerization in the presence of such solvents and reagents.

As used herein, the term "inert solvent" refers to any solvent which does not react chemically with any of the reactants or products of the reaction and which also is incapable of inducing or promoting polymerization of the monomer. For example, it has been discovered that the monomer can undergo some degree of polymerization in the presence of basic solvents. Accordingly, solvents useful in the present invention are preferably neutral or slightly acidic or at least are of a basicity insufficient to induce or promote polymerization of 2-methylene-1,3-propanediamide under the β-elimination reaction conditions being utilized. Similarly, such solvents should be substantially free of any impurities which may induce or promote polymerization of the monomer. For example, water is a protic material which can induce polymerization as well as add across the double bond. Thus, in general, the solvents employed herein should be substantially anhydrous. It may be noted, however, that a minimal amount of water may be present in the reaction solvent system and may be introduced therein, for example, as the water of hydration of a fluoride salt. Such a minimal amount of water may facilitate the reaction by aiding in the solubilization of the fluoride salt in the aprotic solvent.

As used herein, the term "aprotic solvent" refers to any solvent which is substantially incapable of acting as a proton donor or as an acid. Thus, these solvents will generally be incapable of reacting with 2-methylene-1,3-propanediamide or inducing polymerization thereof. Preferred aprotic solvents are those possessing a relatively high dielectric constant. Since the β-elimination reaction is generally believed to involve some degree of charge formation within the starting material, i.e. a partial positive charge formation on the silicon atom and a partial negative charge formation on the leaving group X, the reaction can be expected to proceed more readily in solvents which are able to promote and accommodate such charge formation. Aprotic solvents possessing a high dielectric constant will, of course, more readily accommodate such charge formation than will lower dielectric constant solvents and, thus, are preferred for use in the present invention. In general, the preferred aprotic solvents are those with a dielectric constant at room temperature of at least 15. Such preferred aprotic solvents include, for example, nitrated solvents such as nitromethane, nitroethane, and nitrobenzene; nitriles such as acetonitrile, propionitrile, and benzonitrile; ketones such as acetone and methylethylketone; amides such as formamide, N,N-dimethylformamide, N,N-dimethylacetamide and 1-methyl-2-pyrrolidinone; dimethylsulfoxide; and hexamethylphosphoramide. Dielectric constants of various aprotic solvents can be had by reference to Riddick and Bunger, *Techniques of Chemistry*, Vol. II, Organic Solvents, 3d. ed., John Wiley and Sons, Inc., 1970.

It will be appreciated that certain aprotic solvents, otherwise suitable for use in the present invention, do not readily solvate ionic compounds such as fluoride salts. As noted previously, minimal amounts of water may be utilized to aid in solubilizing a fluoride salt in an aprotic solvent. In addition, as disclosed in U.S. Pat. Nos. 3,562,295, issued Feb. 9, 1971; 3,687,978, issued Aug. 29, 1972; and 4,001,212, issued Jan. 4, 1977, certain macrocyclic multidentate compounds, i.e., compounds having a macrocyclic structure comprising donor or liganding heteroatoms capable of complexing a cation, can be used to solubilize ionic compounds in aprotic solvents. Thus, fluoride salts can be solubilized in aprotic solvents by macrocyclic multidentate compounds capable of complexing the cationic segment of the salt. It has been found that fluoride anion provided by fluoride salts solubilized in an aprotic solvent by a macrocyclic multidentate compound can be used as an initiating agent in the present invention. In a preferred embodiment of the present invention, the β-elimination reaction is initiated by fluoride anion provided by potassium fluoride solubilized in acetonitrile by the macrocyclic multidentate compound dicyclohexyl-18-crown-6 having the structure

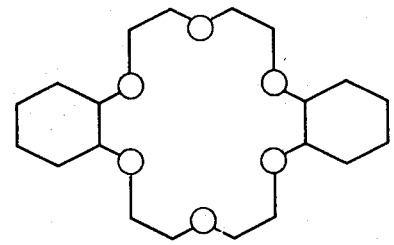

Dicyclohexyl-18-crown-6 is believed to complex the potassium cation of potassium fluoride thus rendering the fluoride anion available to function as the β-elimination initiating agent.

It will be appreciated that other inorganic salts of fluorine, such as sodium fluoride, as well as organic salts of fluorine such as tetramethylammonium fluoride, tetraethylammonium fluoride, tetrapropylammonium fluoride, and tetrabutylammonium fluoride can also be solubilized in aprotic solvents by macrocyclic multidentate compounds. Both two and three dimensional macrocyclic compounds comprising liganding heteroatoms such as oxygen, nitrogen, and sulfur can be used to solubilize fluoride salts in aprotic solvents to provide the fluoride anion initiating agent of the present invention. In general, only a catalytic amount of the macrocyclic multidentate compound is necessary but greater quantities may be added as necessary to satisfactorily dissolve the fluoride salt or to achieve satisfactory reaction times.

Though it is not essential, the β-elimination reaction may be conducted under an inert atmosphere, such as nitrogen. In addition, the introduction of a continuous stream of an inert gas may aid the reaction by removing the relatively low boiling silyl derivatives, formed as a result of the elimination of the silyl group from the starting material, from the reaction solution.

Subsequent to formation, the monomer may, if desired, be isolated from the reaction mixture in any convenient manner as, for example, by filtration of insoluble materials followed by evaporation of the solvent, preferably under vacuum at room temperature. Further purification may be achieved by trituration or recrystallization of the monomer as described in the examples given herein.

The starting materials used in the present invention may be prepared, for example, by abstraction of the proton substituted at the 2-position of a 2-(trisubstituted silyl)methyldiamide and substitution therefor of the desired leaving group. Thus, sulfuryl chloride may be used to prepare a useful starting material wherein X is chloride:

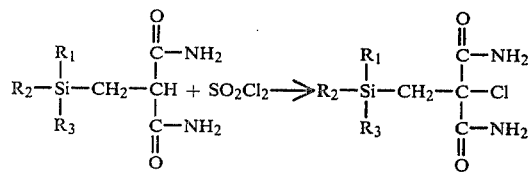

Similar proton abstraction and leaving group substitution may be achieved with other reactive species to produce materials having different leaving groups X. For example, bromination with molecular bromine or N-bromosuccinimide may be used to prepare a material wherein X is bromide. Reaction with lead tetraacetate or p-toluenesulfonyl chloride may be used to produce starting materials wherein X is, respectively, acetate or p-toluenesulfonyl.

The 2-(trisubstituted silyl)methyl-1,3,propanediamide shown in the above sulfuryl chloride reaction can be prepared, for example, by reaction of the corresponding diester of a 2-(trisubstituted silyl)methylpropanedioic acid with ammonia in methanol which contains a catalytic amount of sodium methoxide. The diester of a 2-(trisubstituted silyl)methylpropanedioic acid in turn can be prepared by reaction of the diester of propanedioic acid with an appropriate halomethylsilane in the presence of a base which is incapable of hydrolyzing the ester function. Thus, the following sequence of reactions can be used:

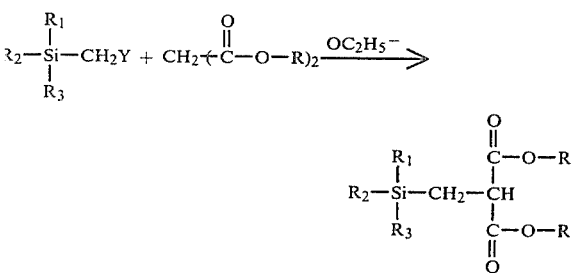

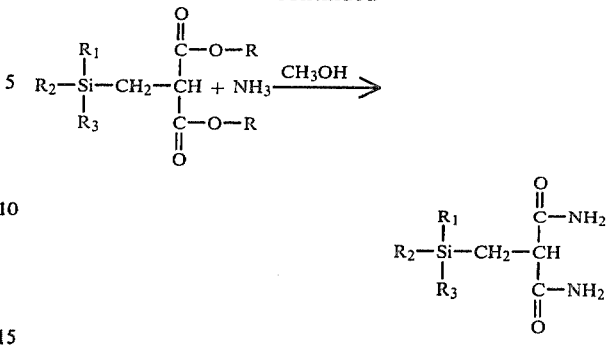

wherein Y is a halogen.

The following examples are given to further illustrate the present invention and are not intended to limit the scope thereof.

EXAMPLE 1

Preparation of 2-chloro-2-(trimethylsilyl)methyl-1,3-propanediamide 47 grams of 2-(trimethylsilyl)methyl-1,3-propane diamide were placed into a 3-necked, 3-liter flask fitted with a mechanical stirrer, dropping funnel, condenser, and drying tube filled with a dessicant. One liter of dry toluene was added and the reaction mixture allowed to stir at room temperature for one hour. One equivalent (20 ml.) of freshly distilled sulfuryl chloride was dissolved in one liter of toluene and this solution added dropwise to the above reaction mixture.

After the addition was completed, the reaction mixture was stirred at room temperature for about 18 hours. The reaction mixture was then suction filtered and the recovered solid washed with 100 ml. of cold toluene. The solid was then air dried.

The solid was recrystallized from about 250 ml. of tetrahydrofuran. Precipitation was aided by the slow addition of about 25 ml. of petroleum ether. The recrystallized product was suction filtered, washed with cold petroleum ether and air dried to give 41.7 grams of white solid melting at 128° C.

Elemental analysis calculated for $C_7H_{15}ClN_2O_2Si$: C, 37.75; H, 6.8; Cl, 16.05; N, 12.39. Found: C, 38.06; H, 7.2; Cl, 15.91; N, 12.58.

EXAMPLE 2

Preparation of 2-methylene-1,3-propanediamide 44.4 grams of 2-chloro-2-(trimethylsilyl)methyl-1,3-propanediamide were added to 3 liters of acetonitrile and stirred for one hour. Undissolved solids were removed by filtration. The solution was then placed in a 5-liter flask fitted with a drying tube filled with calcium chloride. 1.3 equivalents (24.4 grams) of potassium fluoride dihydrate and about 0.3 grams of dicyclohexyl-18-crown-6 were added and the reaction mixture stirred at a temperature of about 25° C. until nuclear magnetic resonance analysis indicated the absence of starting material.

The mixture was filtered and the solid obtained was washed with 1.5 liters of acetonitrile to remove monomer from the solid paste. The combined acetonitrile solutions were dried over magnesium sulfate and evaporated under vacuum at room temperature to give a white solid. This solid was triturated with methylene chloride until remaining traces of starting material were removed. The solid product was then dissolved in 2.5 liters of acetone, undissolved materials were filtered, and the acetone solution was concentrated under vacuum to give 16 grams of solid product. This product was recrystallized from a mixture of 1800 ml. of ethylacetate and 600 ml. of petroleum ether to give 12.7 grams of product melting at 149°–151° C.

2-methylene-1,3-propanediamide is useful in preparing polymers which can be used in preparing coating compositions, films, and filaments.

What is claimed is:

1. A process for preparing 2-methylene-1,3-propanediamide which comprises:

providing a solution of a compound of the formula

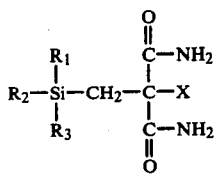

wherein $R_1$, $R_2$, and $R_3$ can each independently be lower alkyl of from 1 to 10 carbon atoms, aryl, alkaryl, aralkyl, or halogen, and X is an electron-accepting leaving group, in an inert, aprotic organic solvent;

subjecting said compound in said solution to fluoride anion to effect elimination of the silyl group

and the electron-accepting leaving group

from said compound to form a double bond between those carbon atoms to which the silyl group and the electron-accepting leaving group were bonded, thereby forming 2-methylene-1,3-propanediamide.

2. A process of claim 1 wherein each of $R_1$, $R_2$, and $R_3$ is lower alkyl of from 1 to 10 carbon atoms.

3. A process of claim 2 wherein each of $R_1$, $R_2$, and $R_3$ is methyl.

4. A process of claim 1 wherein X is chloride.

5. A process of claim 1 wherein the molar ratio of said fluoride anion to said compound is about 0.1:1.0 to about 2.0:1.0.

6. A process of claim 5 wherein the molar ratio of fluoride anion to said compound is about 1.1:1.0 to about 1.5:1.0.

7. A process of claim 1 wherein said 2-methylene-1,3-propanediamide is formed at a reaction temperature of about 15° C. to about 50° C.

8. A process of claim 7 wherein said 2-methylene-1,3-propanediamide is formed at a reaction temperature of about 20° C. to about 35° C.

9. A process of claim 1 wherein the dielectric constant at room temperature of said inert, aprotic organic solvent is at least 15.

10. A process of claim 1 wherein said fluoride anion is provided by dissolving in said inert, aprotic organic solvent an organic or inorganic fluoride salt capable of ionizing therein to provide fluoride anion.

11. A process of claim 10 wherein said organic or inorganic fluoride salt is solubilized in said inert, aprotic organic solvent by a macrocyclic, multidentate compound.

12. A process of claim 10 wherein said inorganic fluoride salt is an alkali metal fluoride.

13. A process of claim 10 wherein said organic fluoride salt is a tertiary ammonium fluoride.

14. A process of claim 11 wherein said macrocyclic multidentate compound is dicyclohexyl-18-crown-6.

15. A process of claim 14 wherein said inorganic fluoride salt is potassium fluoride.

16. A process of claim 15 wherein the dielectric constant at room temperature of said inert, aprotic organic solvent is at least 15.

17. A process of claim 16 wherein said inert, aprotic organic solvent is acetonitrile.

* * * * *